United States Patent
Tzachev (10) Patent No.: US 12,036,329 B2
(45) Date of Patent: Jul. 16, 2024

(54) MUCOADHESIVE DISPERSION NANOPARTICLE SYSTEM AND METHOD FOR PRODUCTION THE SAME

(71) Applicant: LEAD BIOTHERAPEUTICS LTD, Sofia (BG)

(72) Inventor: Christo Tzachev Tzachev, Sofia (BG)

(*) Notice: Subject to any disclaimer, the term of this patent is extended or adjusted under 35 U.S.C. 154(b) by 418 days.

(21) Appl. No.: 17/274,197

(22) PCT Filed: Sep. 11, 2018

(86) PCT No.: PCT/IB2018/001073
§ 371 (c)(1),
(2) Date: Mar. 8, 2021

(87) PCT Pub. No.: WO2020/053609
PCT Pub. Date: Mar. 19, 2020

(65) Prior Publication Data
US 2021/0353553 A1 Nov. 18, 2021

(51) Int. Cl.
| | |
|---|---|
| *A61K 9/51* | (2006.01) |
| *A61K 9/00* | (2006.01) |
| *A61K 9/10* | (2006.01) |
| *A61K 45/06* | (2006.01) |
| *A61K 47/38* | (2006.01) |
| *A61P 11/02* | (2006.01) |
| *A61K 31/4174* | (2006.01) |
| *A61K 31/58* | (2006.01) |
| *B82Y 5/00* | (2011.01) |

(52) U.S. Cl.
CPC .......... *A61K 9/5123* (2013.01); *A61K 9/0043* (2013.01); *A61K 9/006* (2013.01); *A61K 9/10* (2013.01); *A61K 45/06* (2013.01); *A61K 47/38* (2013.01); *A61P 11/02* (2018.01); *A61K 31/4174* (2013.01); *A61K 31/58* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 4,603,131 A | 7/1986 | Bernstein et al. | |
| 5,976,573 A | 11/1999 | Kim | |
| 6,319,513 B1 | 11/2001 | Dobrozsi | |
| 8,242,165 B2 | 8/2012 | Dash et al. | |
| 2014/0079785 A1* | 3/2014 | Jensen | A61P 17/00 514/180 |
| 2015/0359738 A1 | 12/2015 | Mulvahill | |

FOREIGN PATENT DOCUMENTS

| | | | |
|---|---|---|---|
| CN | 103784421 A | * | 5/2014 |
| WO | 9938492 A1 | | 8/1999 |
| WO | 2007049102 A1 | | 5/2007 |
| WO | 2007125134 A1 | | 11/2007 |
| WO | 2009141388 A1 | | 11/2009 |
| WO | 2013188979 A1 | | 12/2013 |
| WO | 2017075565 A1 | | 5/2017 |
| WO | 2017097783 A1 | | 6/2017 |

OTHER PUBLICATIONS

Kheradmandnia et al. (International Journal of Molecular Science, 2016). (Year: 2016).*
ISR; European Patent Office; NL; Apr. 23, 2019.
Ahuja A; Khar RK; Ali J, "Mucoadhesive drug delivery systems", Drug Dev Ind Pharm., (19970000), vol. 23, doi:doi:10.3109/03639049709148498, pp. 489-515, XP008018741.
Schneider CS; Xu Q; Boylan NJ et al., "Nanoparticles that do not adhere to mucus provide uniform and long-lasting active substance delivery to airways following inhalation", Science Advances, (20170000), vol. 3, No. 4, p. e1601556.
Boatsman JE; Calhoun KH; Ryan MW, "Relationship between rhinosinusitis symptoms and mucociliary clearance time", Otolaryngol. Head Neck Surg., (20060000), vol. 134, doi:doi:10.1016/j.otohns.2005.10.045, pp. 491-493, XP025070086.
N. Nafee, K. Forier, K. Braeckmans, M. Schneider, "Mucus-penetrating solid lipid nanoparticles for the treatment of cystic fibrosis: Proof of concept, challenges and pitfalls".

* cited by examiner

*Primary Examiner* — Melissa S Mercier
(74) *Attorney, Agent, or Firm* — Patshegen IP; Moshe Pinchas (57) ABSTRACT

The invention relates to mucoadhesive dispersion nanoparticle system applicable in pharmacy, medicine and cosmetics, especially by administration to surfaces with intensive physiological clearance such as nasal, pulmonal, ocular, oral, throat, rectal, vaginal etc. surfaces, as well as to the method for production such mucoadhesive dispersion nanoparticle system. The composition of mucoadhesive dispersion nanoparticle system comprising in an aqueous medium 0.01 to 2.00 w % hydroxypropyl methyl cellulose and from 0.10 to 10 w % dispersed solid lipid nanoparticles (SLN) for intracellular release of active substances. The advantages of the composition of SLN mucoadhesive dispersion nanoparticle system of the invention are an increased efficacy and controllable depo-effect for transport and delivery of active substances, forming of a continuous film over the applied epithelial surface and substantially increasing of the retention time of the applied dose.

8 Claims, 4 Drawing Sheets

Fig. 7 ature of the parties. The mucosal

MUCOADHESIVE DISPERSION NANOPARTICLE SYSTEM AND METHOD FOR PRODUCTION THE SAME

TECHNICAL FIELD

The invention relates to mucoadhesive dispersion nanoparticle system applicable in pharmacy, medicine and cosmetics, especially by administration to surfaces with intensive physiological clearance such as nasal, pulmonal, ocular, oral, throat, rectal, vaginal etc. surfaces, as well as to the method for production such mucoadhesive dispersion nanoparticle system.

BACKGROUND ART OF THE INVENTION

It is known that the main obstacle before effective penetration and absorption of therapeutic particles is the mucosal barrier, which physiologically scavenges entrapped particulates of the active substance. There are many scientific publications, patent applications and patents describing adhesive delivery systems intended to overcome the physiological clearance of applied medicaments. Mucoadhesion is the most widely used approach due to the better efficacy of therapies. Many mucoadhesive drug delivery systems have been developed for oral, buccal, nasal, rectal and vaginal routes for both systemic and local effects (Ahuja A, Khar R K, Ali J. Mucoadhesive drug delivery systems. Drug Dev Ind Pharm. 1997; 23:489-515). The formulation of mucoadhesive drug delivery system depends on selection the suitable polymer. It is known that the mucoadhesive polymers have numerous hydrophilic groups, such as hydroxyl, carboxyl, amide, and sulfate. These groups attach to mucus or the cell membrane by various interactions such as hydrogen bonding and hydrophobic or electrostatic interactions. These hydrophilic groups also cause polymers to swell in water and, thus, expose the maximum number of adhesive sites.

Different liquid mucoadhesive systems are known and used for preparation of conventional pharmaceutical forms. Such mucoadhesive systems are prepared by adding to the liquid pharmaceutical medium a various mucoadhesive compounds, viscosity enhancers, as for example a water-soluble C1-C4 alkyl-cellulose derivatives, such as HPMC. Mucoadhesive compounds may be useful to provide prolonged adhesion, and so improved efficacy, of pharmaceutically active ingredients in the treatment of a mucosal tissue. /U.S. Pat. Nos. 5,976,573; 6,319,513; 4,603,131, WO9938492; WO2007049102/

Different mucoadhesive/non adhesive particulate systems for delivery of active substances developed to overcome the mucociliary clearance have been described in literature and patent applications.

WO2009141388 describes mucoadhesive composition, adapted for preventing and/or treating a pathological reaction of the immune system of an individual, by inducing a specific tolerance towards at least one antigen involved in said pathological reaction. The composition comprising chitosan particles loaded with said at least one antigen involved in the pathological reaction, wherein the size of the loaded chitosan particles is of more than 800 nm. Particle of chitosan has positive charge and they are mucoadhesive.

WO2013188979 describes mucoadhesive nanoparticle delivery system. The nanoparticles are formed from amphiphilic macromolecules conjugated to a mucosal targeting moiety in such a manner that the surface of the nanoparticle is coated with the targeting moiety. The surface density of the targeting moiety can be tuned for adjustable targeting of the nanoparticles to a mucosal site without substantially compromising the stability of the particles. The mucosal targeting moiety is selected from a phenylboronic acid derivative, a thiol derivative or an acrylate derivative, wherein at least a portion of said functional moieties of the hydrophilic portion are conjugated to the mucosal targeting moiety. The particles were found to have high loading efficiency and sustained release properties at the mucosal site.

WO2017075565 describes polymeric nanoparticles as mucus penetrating particles (MPP) coated with one or more surface modifying agents. The surface modifying agents coat the surface of the particle in a sufficient density to enhance the diffusion of the modified nanoparticles throughout the mucosa, relative to equivalent nanoparticlesthat are not surfacemodified. Nanoparticles can be sufficiently densely coated with poly(ethyleneglycol) (PEG) with a molecularweight of from 10 kD to 40 kD.

U.S. Pat. No. 8,242,165 describes mucoadhesive nanoparticles for a localized or targeted delivery of taxanes and other active substances as analgesics (e.g., morphine and morphine congeners, opioid analgesics, non-opioid analgesics, and the like) to subjects suffering from cancer. The nanoparticles are formed of a hydrophobic core and a hydrophilic surface layer surrounding the hydrophobic core. The hydrophobic core comprises of glyceryl mono fatty acid esters, in liquid or in solid state, while the hydrophilic surface layer includes chitosan. The nanoparticles can include emulsifiers (e.g., polyvinyl alcohol) in amount from about 0.1% to about 5% and/or acids (e.g. citric acid) which may be used in their preparation. The mucoadhesive nanoparticles for a localized or targeted delivery have diameters of less than about 5000 nm and a spherical or elliptical form. The nanoparticles, according to the invention, have mucoadhesive properties, which are due to chitosan shell of solid lipid nanoparticles. The mucoadhesive compound increases the effect of the therapeutic agent on cancer cells in the sample but this increased therapeutic effect is due to the nanoparticles' interaction with increased (relative to the non-cancer cells) levels of mucin on and/or around the cancer cells. The functionalized shell gives targeting to the liver and mucoadhesive properties allowing the particles to attach to mucus glycoproteins and cell membranes.

Investigating mucoadhesive particles (MAP), Schneider found that regardless of particle diameter, were rapidly removed from the lumen of the lung in vivo. This suggests that previously reported favorable outcomes achieved with an active substance in MAP compared to carrier-free soluble active substance formulations may be partly attributed to the benefits intrinsic to particle-based active substance delivery systems rather than particle mucoadhesion per se. In contrast, the author describes liposome-based mucus-penetrating particles (MPP) uniformly distributed throughout the airway mucus layer and exhibited improved retention, resulting in improved therapeutic efficacy compared to carrier-free active substance and active substance delivered by a MAP formulation. These findings suggest that MPP, at least those up to 300 nm in diameter, provide an attractive alternative to the use of MAP to enhance pulmonary delivery of therapeutics. (Schneider C S, Xu Q, Boylan N J, et al. Nanoparticles that do not adhere to mucus provide uniform and long-lasting active substance delivery to airways following inhalation. Science Advances. 2017; 3(4):e1601556. doi:10.1126/sciadv. 1601556.) WO2007125134 relates to the formulation of liposomal vesicles in aqueous solutions with tear film characteristics. The pharmaceutical liposomal system uses phosphatidylcholine whose transition temperature is lower than the temperature of the corneal surface and also incorporates mucoadhesive and/or mucomimetic polymers or substances (mucin or polymers such as hyaluronic acid, cellulose derivatives, chondroitin sulphate, chitosan, colominic acid, thiolic derivatives or other similar components). The liposomes have average particle diameters varied from 392 to 478 nm.

It is also known that solid lipid particulate systems such as solid lipid nanoparticles (SLN) and lipid microparticles (LM) are alternative carriers for transport and delivery of active compounds. They are advantageous for many different administration routes and the field of application particularly depends on the type of incorporated active substance. The active substances are typically encapsulated in a lipid matrix which is biodegradable and/or biocompatible. The active substance release can occur as a result of diffusion, dissolution and/or matrix degradation. Furthermore, these systems can deliver active substance to specific tissues and provide controlled release therapy. Such a targeted and sustained active substance delivery can decrease the active substance related toxicity and increase patient's compliance with less frequent dosing.

In 2017 N. Nafee described Poloxamer-, Tween- and PVA-coated SLNs that showed faster diffusion rate in mucus (N. Nafee, K. Forier, K. Braeckmans, M. Schneider, Mucus-penetrating solid lipid nanoparticles for the treatment of cystic fibrosis: Proof of concept, challenges and pitfalls, European Journal of Pharmaceutics and Biopharmaceutics (2017). WO2017097783 is directed to an immunogenic composition comprising SLNs, wherein the SLNs comprise an aminoalkyl glucosaminide phosphate (AGP). Preferred lipids for use in the present invention are behenates of glycerol. In some embodiment of the invention SLNs are cationic. Cationic SLNs can e.g. potentially allow mucoadhesion by their electrostatic interaction with polyanionic mucin coating on the sublingual mucosa. In other embodiments, the SLNs are SLNs coated with methylglycol chitosan. The average size of the SLNs in the composition is between 30 and 200 nm. The composition is administered via a transmucosal route, such as sublingual administration.

There are no known compositions of solid lipid nanoparticles in mucoadhesive carrier intended to allow prolonged stay of the composition on epithelial surfaces including mucus layers so that the particles to completely penetrate through layers and to be fully absorbed.

DISCLOSURE OF INVENTION

The aim of the invention is to create safe mucoadhesive dispersion nanoparticle system with increased efficacy and with controllable depo-effect for transport and delivery of active substances, incorporated in SLN, which system to be able to form a continuous film over the applied epithelial surface, to have low viscosity and high adhesiveness, to lack of toxicity and to be compatible with the dispersed SLN, which SLN possess high lipophilicity and extremely low (or lack of) in-vitro dissolution profile, as to preserve the active substance within the dispersion and to indicate both lipase-resistance and ability to freely penetrate through cell membranes into cells, where to release the active substance (s) by an intracellular erosion, by using a simplified and effective method for its production.

The aim of the invention is achieved by formulation of mucoadhesive dispersion nanoparticle system, comprising in an aqueous medium containing 0.01 to 2.00 w % hydroxypropyl methyl cellulose and from 0.10 to 10 w % dispersed solid lipid nanoparticles (SLN) for intracellular release of active substances, where the said dispersion of SLN contains nanoparticles with a diameter from 15 to 100 nm, which nanoparticles comprising from 20 to 99 w/w parts a solid lipid selected from the group of natural plant or synthetic waxes, from 0.01 to 20 w/w parts d-α-Tocopheryl polyethylene glycol 1000 succinate (TPGS), red palm oil concentrate with content of 30% tocotrienols in an amount up to 20 w % of the total lipid and from 0.00001 to 70 w/w parts of an incorporated in their core active substance.

The hydroxypropyl methyl cellulose of mucoadhesive dispersion nanoparticle system, according to the invention, have a viscosity of from 2500 to 5500 cps (mPa.$), preferably more than 3000 to less than 5000 cps (mPa.$), more preferably from 3200 to 4800 cps (mPa.$), (Ubbelohde, 2 wt % solution in water, 20° C., in accordance with USP). Its aqueous solution forms a mucoadhesive carrier intended to allow prolonged stay of the composition on epithelial surfaces including mucus layers so that the particles to completely penetrate through layers and to be fully absorbed.

The mucoadhesive dispersion nanoparticle system can include in addition buffers, isotonic salts and preservatives.

In a preferred embodiment, the composition of the SLN of the mucoadhesive dispersion nanoparticle system contains as the natural plant wax carnauba wax. This natural wax is preferable because of lower crystallinity related with composition complexity. Carnauba wax is preferable, because being the hardest among plant waxes. It is resistant to enzyme degradation in the gastro-intestinal tract and intercellular spaces, because it has long chain hydrocarbons composition, and weak cross linking. Carnauba wax is capable to transport active substances in intact state into the cells. Besides carnauba wax doesn't form protein corona with human albumin and other soluble proteins within the human body in contrast with many other lipids.

The inclusion of lipid red palm oil concentrate with contents of 30% tocotrienols in the matrix of the solid lipid nanoparticle (SLN) is a preferred embodiment of the invention. As a liquid lipid can be used, also, other lipids, as natural and synthetic oil with high content of Tocotrienol, such as rice bran oil, wheat germ oil, or animal oils. The liquid lipid in current invention serves to partially weaken the strong crystal structure of carnauba wax in order to increase its capacity for incorporation of the active substance. The amount of liquid lipid must not exceed the threshold of formation of liquid domains within the lipid particle. This threshold is dynamic and except the liquid lipid amount, it depends on the nature and amount of the rest of ingredients in the particle composition.

In other embodiment the solid lipid nanoparticle of the mucoadhesive dispersion nanoparticle system, according to the invention includes in the structure of matrix additionally a polysorbate selected from polysorbate 20, polysorbate 40, polysorbate 60 or polysorbate 80. The polysorbate is in an amount from 0.01 to 10 w/w parts. In one preferred embodiment the surface acting agent of the solid lipid nanoparticle of the mucoadhesive dispersion nanoparticle system, according the invention, the polysorbate is polysorbate 40.

It is established that d-α-Tocopheryl polyethylene glycol 1000 succinate (TPGS) is so far the most potential efflux pump inhibitor, while polysorbates were found to significantly increase the apical-to-basolateral and decrease the basolateral-to-apical (BL-AP) permeability, TPGS exhibits a reduction in the BL-AP permeability in Caco-2 monolayers. Polysorbates inhibit the peptide transporter. It then can be speculated that according to literature data a combination of TPGS and polysorbate must express synergistic effect on P-gp inhibition. However, reverse effect could also be regarded as possible due to opposite activities on the membrane fluidity: polysorbates fluidize, but tpgs rigidizes the membrane fluidity. That's why the obviousness of the results of combination between TPGS and polysorbate is excluded.

The dispersion of solid lipid nanoparticles, included in the mucoadhesive dispersion nanoparticle system according to the invention, has the solid lipid nanoparticles with a structure of a matrix for incorporation of active substances, where escaping the active substance release in the body fluids and targeting the cell digestion is achieved by only intracellular but not interstitial, mucosal or digestive system enzyme degradation or by diffusion out of the particle matrix.

Active substance incorporated in the SLN of the mucoadhesive dispersion nanoparticle system, according to the invention, is selected from active substances, and substances used as diagnostic agents, biological products, food supplements, cosmetic products or medical devices.

The mucoadhesive dispersion nanoparticle system according to the invention is prepared by dissolving of hydroxypropyl methyl cellulose in water to form an aqueous solution after that the solution received is added to the cooled down gradually under stirring to 20° C.+/−2° C. dispersion of the solid lipid nanoparticles, which is prepared by mixing of lipid compound, surface acting agent and active substance, the mixture received is heated up to 90° C.+/−2° C. to melt, it is stirred until homogenization after that to the mixture obtained under stirring is added water heated up to 90° C.+/−2° C.

The advantages of the composition of SLN mucoadhesive dispersion nanoparticle system of the invention are:
- increased efficacy and controllable depo-effect for transport and delivery of active substances which allows the single dose of the medication to be decreased at least 20 times, and the daily dose to be decreased 40 to 80 times;
- forming a continuous film over the applied epithelial surface with low viscosity and high adhesiveness;
- substantially increasing of the retention time of the applied dose (87% increase), but not the viscosity (just 1.05 cP increase at 33° C.) by using of a small amount from mucoadhesive polymer;
- the SLN included in the system is non-toxic, has a high lipophilicity and extremely low (or lack of) in-vitro dissolution profile, designates with both lipase-resistance and ability to freely penetrate through cell membranes into cells where to release the active substance (s) by an intracellular erosion;
- the mucoadhesive dispersion nanoparticle system is produced by using a simplified and effective method of its production.

EXAMPLES

Hereinafter, the present invention is described in more detail and specifically with reference to the Examples, which however are not intended to limit the present invention.

Examples 1. Preparation of Mucoadhesive Dispersion Nanoparticle System in Variants with and without Active Substances, According to the Invention A. Preparation of Placebo 1% Mucoadhesive Dispersion Nanoparticle System For the preparation of placebo 1% mucoadhesive dispersion nanoparticle system are used the following compounds: dispersion of solid lipid nanoparticles (SLN)

| Compounds | Amount in w/w parts |
|---|---|
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.70 |
| HPMC | 0.20 |
| Edetic acid disodium salt | 0.50 |
| NaCl | 0.80 |
| Water | up to 100.00 |

For the preparation of dispersion of solid lipid nanoparticles (SLN) are mixed Carnauba wax, Red palm oil concentrate, d-α-Tocopheryl polyethylene glycol 1000 succinate (TPGS) and Polysorbate 40. The mixture is heated up to 90° C.+/−2° C. to melt and stirred until homogeneous clear mixture is obtained. The needed amount of water with the NaCl dissolved in it is heated up to 90° C.+/−2° C. and it is added dropwise to the homogeneous mixture obtained under stirring.

The obtained dispersion is cooled down under stirring to 20° C.+/−2° C. to give the nanoparticle dispersion. The amount of Edetic acid disodium salt is dissolved in dispersion.

0.2 g of HPMC are dissolved in part of the provided water, then filtered through 20-micron filter and finally added to the SLN dispersion to produce mucoadhesive dispersion nanoparticle system.

B. Preparation of 1% Mucoadhesive Dispersion Nanoparticle System with 0.2% Stevia For the preparation of 1% mucoadhesive dispersion nanoparticle system with Stevia are used the following compounds:

| Compounds | Amount in w/w parts |
| --- | --- |
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.70 |
| Stevia | 0.20 |
| HPMC | 0.20 |
| Edetic acid disodium salt | 0.50 |
| NaCl | 0.80 |
| Water | up to 100.00 |

The dispersion of lipid nanoparticles is obtained as per the procedure described in Example 1A. The calculated amount of Stevia is added into the mucoadhesive dispersion nanoparticle system under steering.

C. Preparation of 1% Mucoadhesive Dispersion Nanoparticle System with 0.0025% Mometasone Furoate For the preparation of 1% mucoadhesive dispersion nanoparticle system with 0.0025% Mometasone furoate are used the following compounds:

| Compounds | Amount in w/w parts |
| --- | --- |
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.70 |
| Mometasone furoate | 0.0025 |
| HPMC | 0.20 |
| Edetic acid disodium salt | 0.50 |
| NaCl | 0.80 |
| Water | up to 100.00 |

The dispersion of lipid nanoparticles is obtained as per the procedure described in Example 1A. The calculated amount of Mometasone furoate is added to the lipid mixture before heating.

D. Preparation of 1.0% Mucoadhesive Dispersion Nanoparticle System with 0.0025% Mometasone Furoate/Xylometazoline 0.005%

For the preparation of 1.0% mucoadhesive dispersion nanoparticle system with 0.0025% Mometasone furoate/Xylometazoline 0.005% are used the following compounds:

| Compounds | Amount in w/w parts |
| --- | --- |
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.70 |
| Mometasone furoate | 0.0025 |
| Xylometazoline | 0.005 |
| HPMC | 0.20 |
| Edetic acid disodium salt | 0.50 |
| NaCl | 0.80 |
| Water | up to 100.00 |

The dispersion of lipid nanoparticles is obtained as per the procedure described in Example 1A. The calculated amount of Mometasone furoate and Xylometazoline is added to the lipid mixture before heating.

F. Preparation of 3.0% Mucoadhesive Dispersion Nanoparticle System with 0.1% Loratadine For the preparation of a lipid nanoparticles with 0.1% Loratadine are used the following compounds:

| Compounds | Amount in w/w parts |
| --- | --- |
| Carnauba wax | 3.00 |
| Red palm oil concentrate (30% tocotrienols) | 0.60 |
| d-a-Tocopheryl polyethylene glycol 1000 succinate (TPGS) | 1.50 |
| Polysorbate 40 | 2.10 |
| Loratadin | 0.10 |
| HPMC | 0.20 |
| Edetic acid disodium salt | 0.50 |
| NaCl | 0.80 |
| Water | up to 100.0 |

The dispersion of lipid nanoparticles is obtained as per the procedure described in Example 1A. The calculated amount of Loratadin is added to the lipid mixture before heating.

Example 2. Nasal Mucoadhesiveness Test of Mucoadhesive Dispersion System on Healthy Volunteers For the test is used composition as per Example 1B.
The reference solution 1 (RS1) has the following composition:

| Compounds | Amount in w/w parts |
| --- | --- |
| Stevia | 0.2 |
| Edetic acid disodium salt | 0.5 |
| NaCl | 0.8 |
| Water | up to 100 |

The Reference solution 2 (RS2) has the following composition:

| Compounds | Amount in w/w parts |
| --- | --- |
| Stevia | 0.2 |
| HPMC | 0.2 |
| Edetic acid disodium salt | 0.5 |
| NaCl | 0.8 |
| Water | up to 100 |

The Reference solution 3 (RS3) has the following composition:

| Compounds | Amount in w/w parts |
| --- | --- |
| HPMC | 0.2 |
| Edetic acid sodium salt | 0.5 |

-continued

| Compounds | Amount in w/w parts |
|---|---|
| NaCl | 0.8 |
| Water | up to 100 |

The Reference solution 4 (RS4) has the following composition

| Compounds | Amount in w/w parts |
|---|---|
| Carnauba wax | 1.00 |
| Red palm oil concentrate (30% tocotrienols) | 0.20 |
| d-α-Tocopheryl polyethylene glycol 1000 succinate (TPGS) | 0.50 |
| Polysorbate 40 | 0.70 |
| Edetic acid sodium salt | 0.5 |
| NaCl | 0.80 |
| Water | up to 100.00 |

The composition has been prepared according to the directions described in Example 1A.

Study Subjects

Twelve healthy subjects (8 men) age ranged between 24 and 60, mean 40 years signed informed consent for their participation in the study. None of them suffered from any clinically significant chronic diseases, nor did any of them take medicines on regular basis. None of the subjects was currently smoking and no one had suffered a viral respiratory infection within the past month. ENT examination did not reveal any local structural abnormalities or inflammatory disorders.

Study Design

Assessments were done in separate visits at 7 days apart. During visits double blind randomized comparisons were made between nasal clearance times of mucoadhesive dispersion system and RS solutions of Stevia.

Nasal Clearance Measurements

Nasal clearance of Stevia was done by own modification of the method described by JE Boatsman et al. [Boatsman J E, Calhoun K H, Ryan M W. Relationship between rhinosinusitis symptoms and mucociliary clearance time. Otolaryngol. Head Neck Surg. 2006, 134: 491-493.].

Briefly, 100 μL of the mucoadhesive dispersion system or RS1 or RS2 of Stevia solution were applied via nasal spray with mechanical pump device in the vestibule of both nostrils at which point timing was started. Subjects were instructed to swallow only at the prompt of the investigator performing the chronometry with a stopwatch. After the first minute with the head bending down, subjects were told to straighten up and swallowed every 30 seconds until they sensed sweet taste in their mouth.

Statistical Analysis

Comparison between the continuous variables for each preparation presented as mean+/−SEM were done using paired Student's t-test and Manova. Correlation between objective and subjective measurements were performed using Pearson's correlation coefficient. A two-tailed level of significance of $p<0.05$ was accepted.

Results

Figure 1:
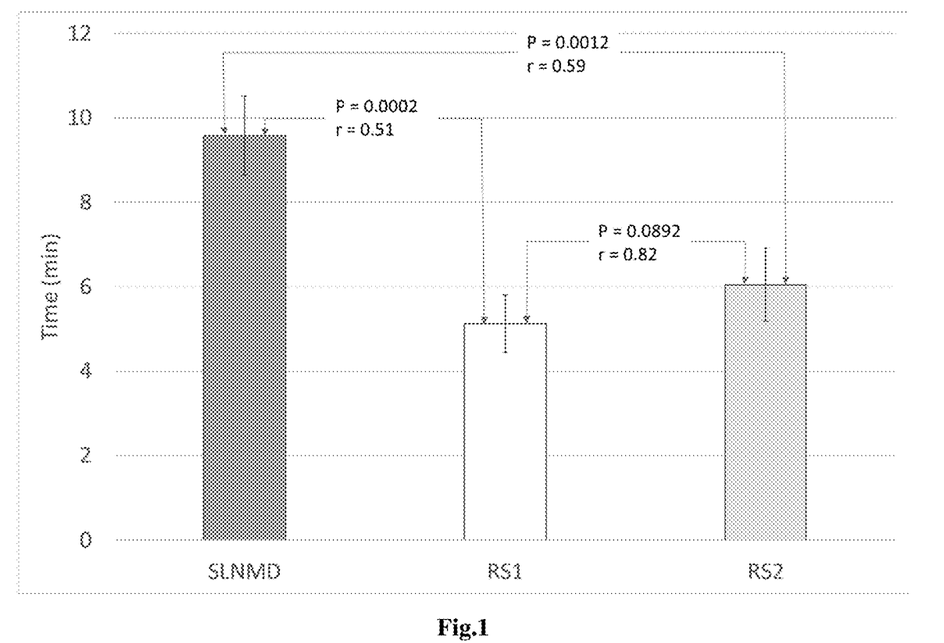
FIG. 1 shows Nasal Clearance Times for SLN Mucoadhesive Dispersion (SLNMD) described as composition in Example 1B compared with the reference solution (RS) of Stevia, described in Example 2. p value represents the level of significance in the difference between Series M and M/X.

Nasal Clearance Times for mucoadhesive dispersion system and RS1 and RS2 are shown in FIG. 1.

All data involving times of nasal clearance complied with the criteria for normal distribution according to the one sample Kolmogorov-Smirnov test.

As shown in FIG. 1, SLNMD expressed delayed clearance time for Stevia compared to RS1 and RS2, 9.58 (±0.94) min vs. 5.13 (±0.69) min. vs 6.04 (±0.68). While the clearance time with RS2, which contains 0.2% HPMC, was not found significantly different from that of RS1, SLNMD, which also contained 0.2% HPMC showed 87% increase compared to RS1 ($p<0.001$). Strong positive correlation was found between RS1 and RS2 (r=0.823) whereas moderate correlation was found between SLNMD and both RS1 and RS2 (r=0.509, resp. 0.585). The delayed clearance of SLNMD suggests that HPMC alone is not the only factor in the composition determining the high Mucoadhesion of SLNMD, but the cumulative effect of dispersion components.

Study Conclusion:

The small amount of mucoadhesive polymer at level of 0.2% increased substantially the retention time of the applied dose (87% increase), but not the viscosity (just 1.05 cP increase at 33° C. for SLNMD).

| Dynamic viscosity of solutions per Examples 1B, 1C, and 2 at 25° C. and 33° C. (n = 6, mean +/− SD), [mPa · s] | | | | | | | |
|---|---|---|---|---|---|---|---|
| 25° C. | | | | 33° C. | | | |
| SLNMD[1] | RS3[2] | RS4[3] | Water | SLNMD[1] | RS3[2] | RS4[3] | Water |
| 2.69 ± 0.0233 | 3.58 ± 0.0049 | 0.99 ± 0.0088 | 0.89 ± 0.0053 | 1.84 ± 0.0089 | 3.04 ± 0.0233 | 0.89 ± 0.0076 | 0.75 ± 0.0067 |

[1]Composition according to Example 1B;
[2]RS3 composition according to Example 2;
[3]RS4 composition according to Example 2

The viscosity measurements are made at two temperature levels, assuming the temperature of storing and temperature within the nasal cavity. The viscosity of SLNMD 2.7 mPa·s at 25° C. is low enough to be easily sprayed from standard spray pump device. The viscosity of 1.8 mPa·s at 33° C. is low enough for fast and easy distribution of the applied dose over a large mucosal surface. The comparison between SLNMD and RS3 at both 25° C. and 33° C. shows significant difference ($p<0.001$) in the viscosity. SLNMD has lower viscosity and higher mucoadhesiveness (nasal mucociliary clearance) from water solutions of HPMC with the same concentration (0.2%). These differences allow SLNMD to flow better, to be easily sprayed, to mix better with the mucus secretions, to cover a larger mucosal surface and to stay longer over the mucosa ensuring higher bioavailability.

Example 3. Clinical Research Studies with Active Substance (s) Loaded on Mucoadhesive Dispersion Nanoparticle System A. Clinical research study of mucoadhesive dispersion nanoparticle system loaded with low dosed mometasone furoate at dose 2.5 mcg per 100 mcl spray.

This clinical study has been developed and designed with the following aims:

To prove the author's original concept for the high effectivity of mucoadhesive dispersion nanoparticle system, loaded with active substances;

To study the effect of a nasal spray, containing lower level of active substance Mometasone furoate, loaded on mucoadhesive dispersion nanoparticle system.

Working Hypothesis

The only possible reduction in the usual therapeutic levels in local corticosteroid therapy of perennial allergic rhinitis is its intracell delivery without any losses within the mucus linings and interstitial spaces. According to the present invention such an effective intracellular delivery is possible only with the use of mucoadhesive dispersion carrier system.

Study Design

Mucoadhesive dispersion nanoparticle system composition of Mometasone furoate was formulated in spray form delivering dose of 2.5 µg/per spray as described in Example 1C.

12 outpatients (8 women and 4 men, aged between 18 and 69 years) at the Department of Immunology and Allergology at the National Center of Infectious and Parasitic Diseases, diagnosed with perennial allergic rhinitis gave informed consent to volunteer for the study and were instructed to spray the preparation twice in each nostril on "as needed" basis but no more than 4 times a day.

The study was designed as open, single medication (no reference product) in two periods, ten days each, with seven days washout. The washout period was used to collect information about expected left-over (depo) effect of the new medication.

The symptoms (except the time for free nasal breathing) were evaluated by Visual Analogue Scale (VAS), ranged between 0 (lack of symptom) and 100 (full expression of the symptom).

The studied symptoms were:
(time for) free nasal breathing after using the spray
secretion from the nose
itching in the nose
nasal congestion
sneezing
eye irritation During the clinical testing, the overall health condition (or condition change) of the patients was observed. Patients were examined initially and after the end of each period. Patients were phone called once daily in line with the measures for strict daily control on medication application and duly recording in patient cards.

Statistical Analysis

Comparison between the continuous variables presented as mean+/−SEM were done using paired Student's t-test and Manova. A two-tailed level of significance of $p<0.05$ was accepted.

Results:

1. Time for Free Nasal Breathing (TFNB)

Figure 2:
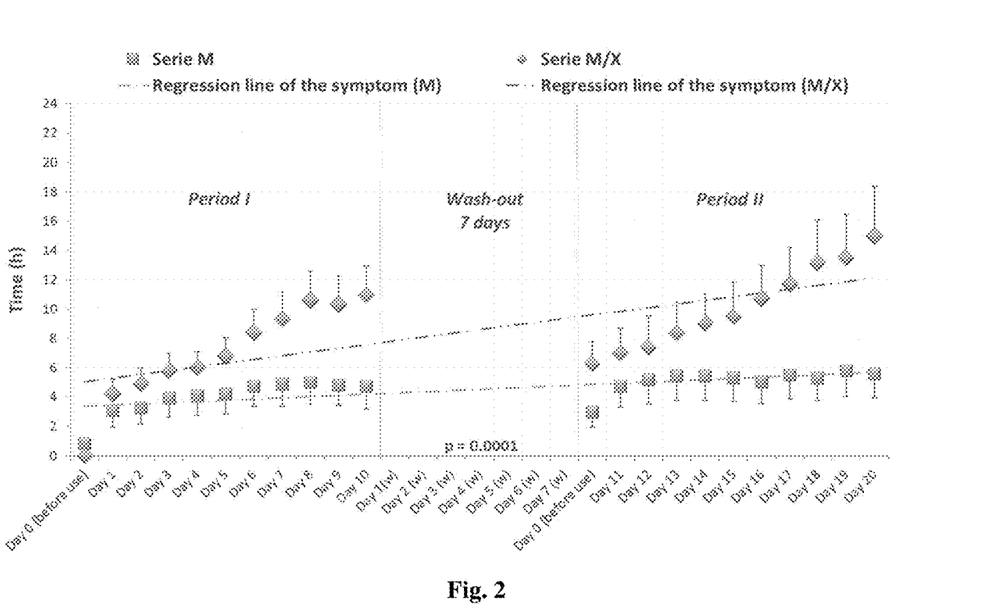
FIG. 2. Time for free nasal breathing (TFNB) after medication with SLNMD loaded with Mometasone, 2.5 mcg (Serie M, n=12, squares) or Mometasone/Xylometazoline, 2.5/5.0 mcg, (Serie M/X, n=17, rhombi), Mean+/−SE. p value represents the level of significance in the difference between Series M and M/X.

The results are shown in FIG. 2, Serie M. Significant improvement in nasal symptom was observed between day 0 (baseline) and day 10 and day 20 (p=0). 5.6 h Mean TFNB was pointed in the patients VAS on day 20 of the study. The TFNB reached duration plateau on day 7 of Period I whereas it was observed as early as on day 3 of Period II. Strong positive correlation (Pearson r=0.92) was found between periods. Left-over effect of 294% above the baseline was observed on day 0 of Period II. No nasal rebound swelling was achieved during the test.

2. Nasal Secretion Score During Medication Periods

Figure 3:
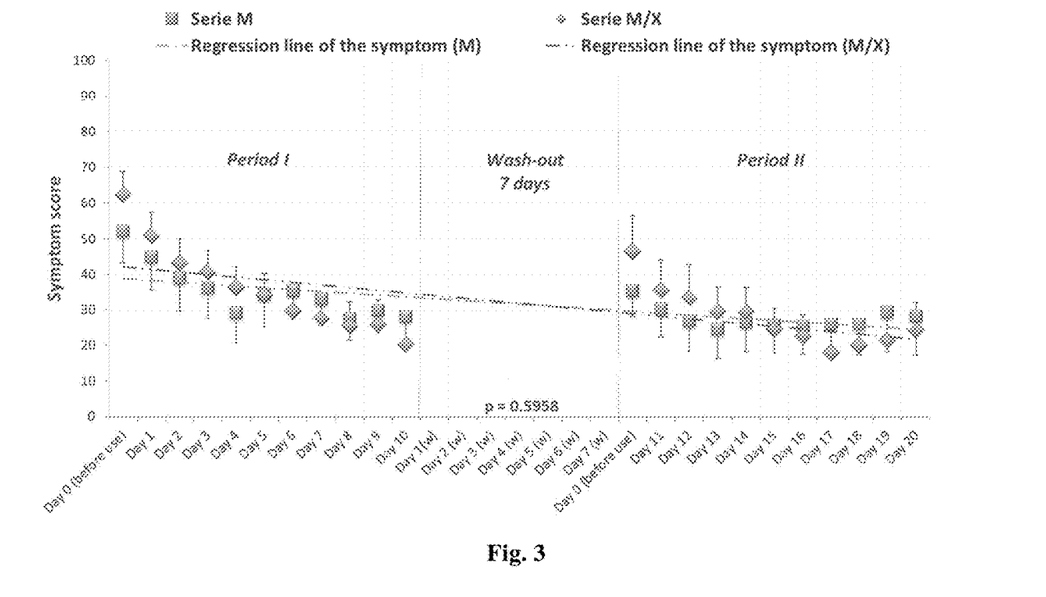
FIG. 3. Nasal secretion score after medication with SLNMD loaded with Mometasone, 2.5 mcg (Serie M, n=12, squares) or Mometasone/Xylometazoline, 2.5/5.0 mcg, (Serie M/X, n=17, rhombi), Mean+/−SE. p value represents the level of significance in the difference between Series M and M/X.

The results are shown in FIG. 3, Serie M. Significant improvement ($p<0.05$) in nasal symptom was observed. The maximum effect was achieved on day 4 of Period I and on day 3 of Period II. Strong positive correlation (Pearson r=0.77) was found between periods. Left-over effect of 32% decrease from baseline was observed on day 0 of Period II.

3. Nasal Itching During the Medication Periods

Figure 4:
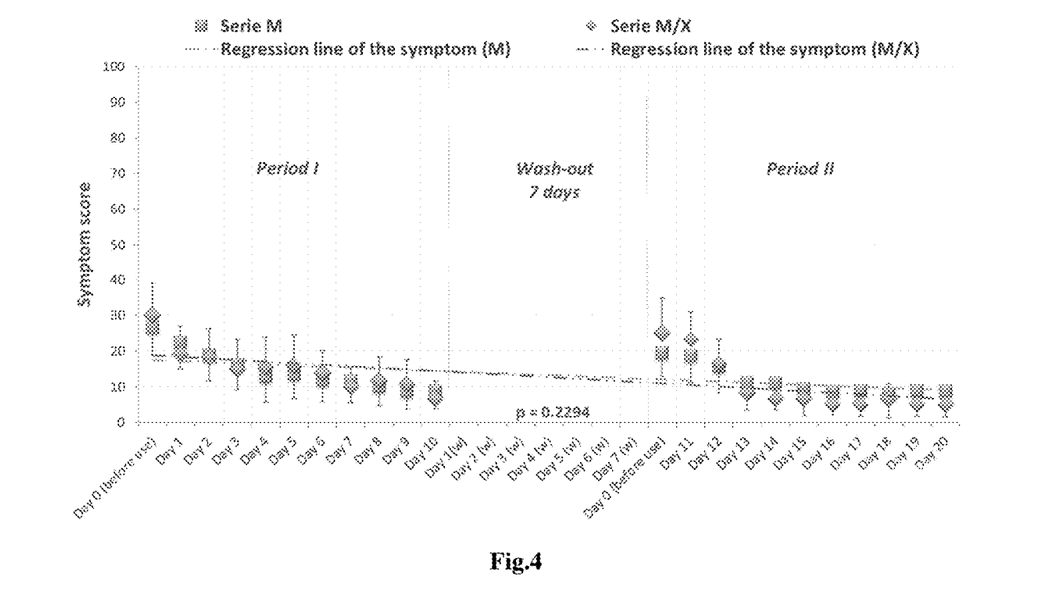
FIG. 4. Nasal itching score after medication with SLNMD loaded with Mometasone, 2.5 mcg (Serie M, n=12, squares) or Mometasone/Xylometazoline, 2.5/5.0 mcg, (Serie M/X, n=17, rhombi), Mean+/−SE. p value represents the level of significance in the difference between Series M and M/X.

The results are shown in FIG. 4, Serie M. Itching practically disappeared through the days of period I. The symptom was gradually decreased until the end of Period I, whereas it reached minimum on day 6 on Period II and remained unchanged. Strong positive correlation (Pearson r=0.83) was found between periods. Left-over effect of 26% decrease from the baseline was observed on day 0 of Period II.

4. Nasal Congestion Score During the Medication Periods

Figure 5:
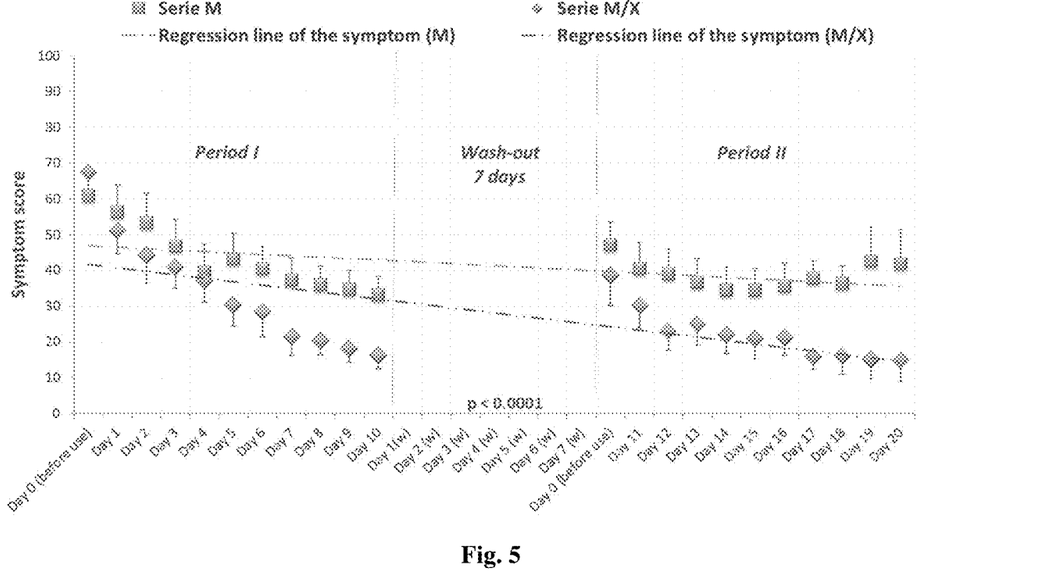
FIG. 5. Nasal congestion score after medication with SLNMD loaded with Mometasone, 2.5 mcg (Serie M, n=12, squares) or Mometasone/Xylometazoline, 2.5/5.0 mcg, (Serie M/X, n=17, rhombi), Mean+/−SE. p value represents the level of significance in the difference between Series M and M/X.

The results are shown in FIG. 5, Serie M. Feeling of nasal congestion was significantly reduced ($p<0.05$) during the medication with 50% reduction of the symptom on day 20. The symptom was gradually decreased during the periods. Moderate positive correlation (Pearson r=0.64) was found between periods. Left-over effect of 23% decrease from the baseline was observed on day 0 of Period II.

5. Sneezing During the Medication Periods

Figure 6:
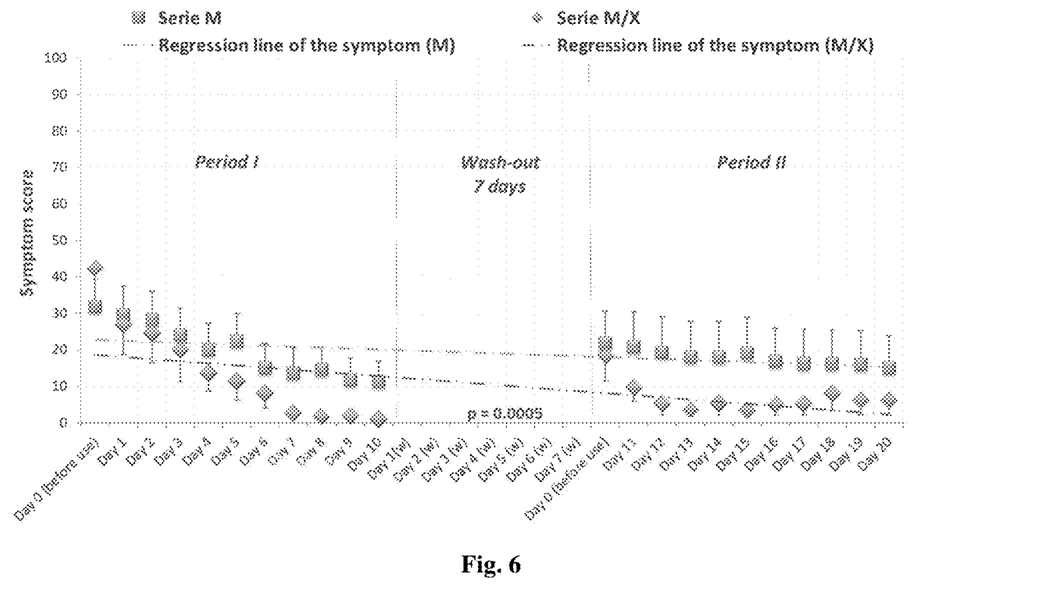
FIG. 6. Sneezing score after medication with SLNMD loaded with Mometasone, 2.5 mcg (Serie M, n=12, squares) or Mometasone/Xylometazoline, 2.5/5.0 mcg, (Serie M/X, n=17, rhombi), Mean+/−SE. p value represents the level of significance in the difference between Series M and M/X.

The results are shown in FIG. 6, Serie M. Sneezing was significantly improved ($p<0.05$) during the course of medication. Gradual decrease was observed during the treatment periods. Moderate positive correlation (Pearson r=0.69) was found between periods. Left-over effect of 31% decrease from the baseline was observed on day 0 of Period II.

6. Eye Irritation During the Medication

Figure 7:
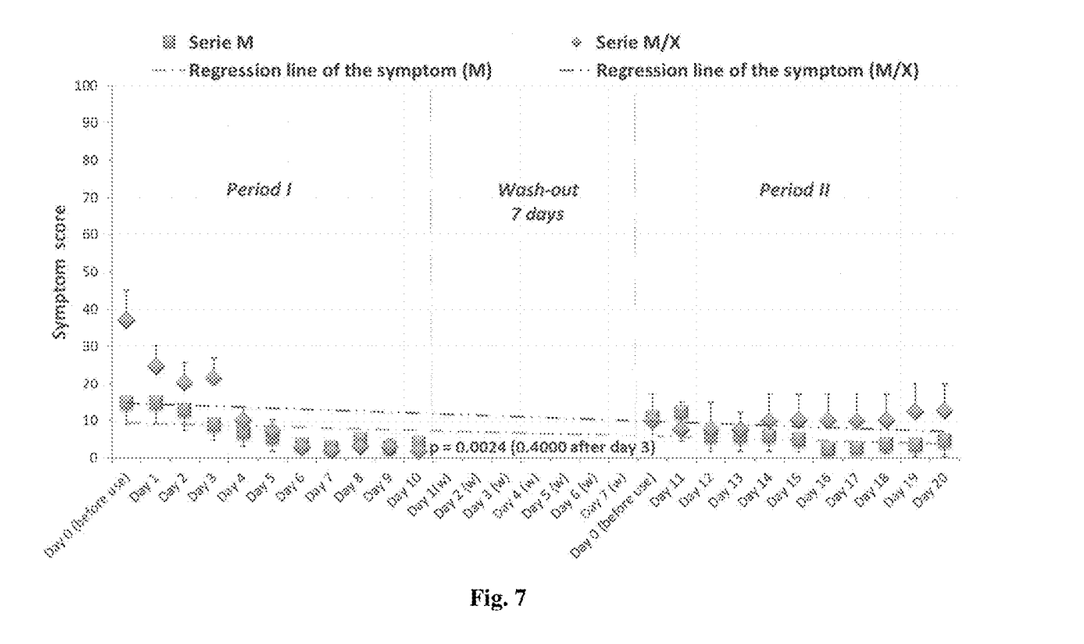
FIG. 7. Eye irritation score after medication with SLNMD loaded with Mometasone, 2.5 mcg (Serie M, n=12, squares) or Mometasone/Xylometazoline, 2.5/5.0 mcg, (Serie M/X, n=17, rhombi), Mean+/−SE. p value represents the level of significance in the difference between Series M and M/X.

The results are shown in FIG. 7, Serie M. Eye irritation was practically eliminated during medication. Moderate positive correlation (Pearson r=0.71) was found between periods. Left-over effect of 93% decrease from the baseline was observed on day 0 of Period II.

Study Conclusion

The study demonstrated high efficacy, left-over (depo) effect of more than 7 days, and excellent tolerability with no adverse effects during the test period of SLNMD of Mometasone furoate at dose 2.5 mcg per spray on the symptoms of perennial allergic rhinitis. No signs of nasal mucosa damage were observed during the last examination after the end of the study.

B. Clinical research study of mucoadhesive dispersion nanoparticle system loaded with a low dosed combination Mometasone furoate/Xylometazoline at dose 2.5 mcg/5 mcg per 100 mcl sprays.

This clinical study has been developed and designed with the following aims:

To prove the author's original concept for high effectivity of low active substance combinations when they are applied to mucous membranes loaded on mucoadhesive dispersion nanoparticle system.

To study the effect of a nasal spray, containing low level of active substance combination Mometasone/Xylometazoline, loaded on mucoadhesive dispersion nanoparticle system.

Working Hypothesis

The only possible reduction in the usual therapeutic levels in local corticosteroid therapy of perennial allergic rhinitis is its intracell delivery without any losses within the mucus linings and interstitial spaces. According to the present invention such an effective intracellular delivery is possible only with the use of mucoadhesive dispersion carrier system.

Xylometazoline boosts the effect of mometasone on rhinitis symptoms. Thus, both active substances can be applied in subtherapeutic dose, ensuring therapeutic effect accompanied with diminished or lack of adverse effects. However, such a synergistic effect has never been observed in sub-dosing. The author's hypothesis for such a synergism is based only on the assumption for application of mucoadhesive dispersion therapeutic system.

Study Design

Mucoadhesive dispersion nanoparticle system composition of Mometasone furoate/Xylometazoline was formulated in spray form delivering dose of 2.5 mcg/5.0 mcg per spray as described in Example 1D.

17 outpatients (10 women and 7 men, aged between 18 and 69 years), at the Department of Immunology and Allergology at the National Center of Infectious and Parasitic Diseases, diagnosed with perennial allergic rhinitis gave informed consent to volunteer for the study and were instructed to spray the preparation twice in each nostril on "as needed" basis but no more than 4 times a day.

The study was designed as open, single medication (no reference product) in two periods, ten days each, with seven days washout. The washout period was used to collect information about expected left-over (depo) effect of the new medication and on the other hand—to observe for eventual rebound swelling after the day 7 usually related with use of the decongestant.

The symptoms were evaluated by Visual Analogue Scale (VAS), ranged between 0 (lack of symptom) and 100 (full expression of the symptom).

The studied symptoms were:

(time for) free nasal breathing after using the spray
secretion from the nose
itching in the nose
nasal congestion
sneezing
eye irritation During the clinical testing, the overall health condition (or condition change) of the patients was observed. Patients were examined initially and after the end of each period. Patients were phone called once daily in line with the measures for strict daily control on medication application and duly recording in patient cards.

Statistical Analysis

Comparison between the continuous variables presented as mean+/−SEM were done using paired Student's t-test and Manova. A two-tailed level of significance of $p<0.05$ was accepted.

Results

7. TFNB

The results are shown in FIG. 2, Serie M/X. Significant improvement in nasal symptom was observed between day 0 and day 10 and day 20 ($p=0$). 15$h$ Mean TFNB was pointed in the patients VAS on day 20 of the study. The TFNB gradually increased during the treatment periods. Strong positive correlation (Pearson $r=0.87$) was found between periods. Left-over effect of 625% above the baseline was observed on day 0 of Period II. No nasal rebound swelling was achieved during the test.

8. Nasal Secretion Score During Medication Periods

The results are shown in FIG. 3, Serie M/X. Significant improvement ($p<0.05$) in nasal symptom was observed. While the symptom score decreased gradually during Period I, it reached its minimum on day 7 of Period II. Strong positive correlation (Pearson $r=0.82$) was found between periods. Left-over effect of 25% decrease from the initial symptom score (day 0, Period I, before treatment) was observed on day 0 of Period II.

9. Nasal Itching During the Medication Periods

The results are shown in FIG. 4, Serie M/X. Itching practically disappeared through the days of period I. The symptom was gradually decreased until day 9 of Period I, whereas it reached minimum on day 4 and remained unchanged until the end of Period II. Weak positive correlation (Pearson $r=0.35$) was found between periods. Left-over effect of 17% decrease from the baseline was observed on day 0 of Period II.

10. Nasal Congestion Score During the Medication Periods

The results are shown in FIG. 5, Serie M/X. Feeling of nasal congestion was significantly reduced ($p<0.05$) during the medication with 78% reduction of the symptom on day 20. The symptom was gradually decreased during the periods. Moderate positive correlation (Pearson $r=0.73$) was found between periods. Left-over effect of 43% decrease from the baseline was observed on day 0 of Period II.

11. Sneezing During the Medication Periods

The results are shown in FIG. 6, Serie M/X. Sneezing was practically eliminated during the course of medication. The minimum of symptom score was reached on day 7 of Period I and on day 2 of Period II. Weak positive correlation (Pearson $r=0.12$) was found between periods. Left-over effect of 57% decrease from the baseline was observed on day 0 of Period II.

12. Eye Irritation During the Medication

The results are shown in FIG. 7, Serie M/X. Eye irritation was practically eliminated during the course of medication. Weak positive correlation (Pearson $r=0.26$) was found between periods. Left-over effect of 73% decrease from the baseline was observed on day 0 of Period II.

Study Conclusion

The study demonstrated high efficacy, left-over (depo) effect of more than 7 days, and excellent tolerability with no adverse effects during the test period of SLNMD of Mometasone furoate/Xylometazoline at dose 2.5 mcg/5.0 mcg per spray on the symptoms of perennial allergic rhinitis. No signs of nasal mucosa damage were observed during the last examination after the end of the study.

C. Explanation of the added value of local sympathomimetic in the low dosed combination Mometasone/Xylometazoline versus monotherapy with Mometasone when used with SLNMD—a comparison between clinical study 3A and 3B.

Both the Series M and M/X significantly increased the TFNB (FIG. 2), still SLNMD loaded with the combination showed faster and 2.5 times longer effect reaching 15 hours at the end of the treatment after a single dose. The significantly higher initial times at day 0 of the Period II compared to the day 0 of Period I relate to long lasting depo effect of SLNMD. During the 7 days wash-out period TFNB with Serie M significantly dropped but still stayed at 294% above the baseline; the same index for Serie M/X was 625% corresponding to more than double the effect of the combination. Serie M reaches a plateau after the day 3 of the tested periods, while the Serie M/X gradually and constantly increased the TFNB reaching 15 hours on day 20. As far as the nasal congestion is one of the down-sides of the corticosteroid monotherapy, it was expected that the combination with decongestant should treat this symptom faster and stronger. What was yet unexpected was the achievement of long lasting effect of more than 7 days with the short acting alfa mimetic xylometazoline (the effect is generally accepted to last up to 5-6 h). There are described methods in the prior art for prolongation the effect of nasally administered active substances with the use of mucoadhesion, but duration of the effect for 7 days and more could not be explained solely with this phenomenon. In fact, the mucoadhesion in the present application has been used to prolong the time for contact of the lipid particles as carriers of the active substance with the nasal mucosa and subsequently to provide high degree of absorption. As digestion of the particles happen within the cells, the only way the absorbed particles to produce effect are intracellular degradation of the lipid and release the free active substance. It is expected that such a transport system will be effective for active substances with intracellular mechanism of action. That's why the choice of corticosteroid (mometasone) is thought reasonable. On the other hand, the high efficacy of xylometazoline delivered within cell was unexpected, yet at levels 20 times lower than the therapeutic ones because its mechanism of action is outer cell membrane alpha-adrenergic receptor mediated. These findings from the clinical tests pointed the author to speculate in two directions:

SLNMD ensures prolonged action in two stages: 1. By Mucoadhesion to reach high bioavailability. 2. By slow degradation within cells, resulting in long lasting (more than 7 days) effect.

Xylometazoline encapsulated in SLNMD shows 20 times (and more) stronger effect due to the high bioavailability and slow degradation of the particles within the cells. Incidents of mucosal ischemia in the course of treatment are unlikely due to the intimate mechanism of active substance delivery: any state of mucosal/cell oxygen insufficiency should strongly decrease mitochondrial function (and vice versa) and consequently slow down particles digestion and AS delivery. This way the delivered amount of the decongestant could be "self-regulated" and never overdosed. This assumption can explain the immediate relief in patients with light to moderate allergic rhinitis and the observed lag in effect in the treatment of more severe states associated with acute inflammation.

The level of significance (p value) for each symptom was calculated (FIGS. 2-7) for Series M and M/X, comparing the data populations. As expected the TFNB and the feeling of nasal congestion showed significant differences with p<0.0001. Unexpectedly the combination gave better control on sneezing (p=0.0005). For the rest of the symptoms significance between the Series was not found.

GENERAL CONCLUSION

The two clinical research studies led the author to make the following general conclusions on the use of the SLNMD system in the treatment of allergic rhinitis:

The use of SLNMD allows the single dose of the medication to be decreased at least 20 times, and the daily dose applications to be decreased 2 to 4 times. This reduction has definite explanation and mechanism of pharmacological action, based on increase in the efficiency by pharmaceutical technology means.

The added value with insertion of sympathomimetic in a subtherapeutic low dose to a low dosed corticosteroid both incorporated in the lipid phase in the SLNMD system consists of highly effective, nontoxic, well tolerable, long lasting medication of allergic rhinitis, completely covering all the symptoms of allergic rhinitis.

The use of corticosteroid in 20 times lower dose then the therapeutic one as well as the use of combination of corticosteroid plus decongestant (xylometazoline) in dose levels at least 20 times lower than the therapeutic ones can only possess detectable therapeutic effect when encapsulated within a special carrier system, such as the one presented in the current application.

The decrease in doses of corticosteroid and decongestant (up to 80 times on a daily base) eliminates the adverse reactions, related with the typical use of the same medications. This is especially important in the pediatrics and in all cases when a long-term therapy, reduction in the adverse reactions and the toxic effects is needed.

The invention claimed is:

1. A mucoadhesive dispersion nanoparticle system comprising:
    an aqueous pharmaceutically acceptable medium and nanoparticles;
        wherein the aqueous medium comprises 0.01 to 2.00 wt. % hydroxypropyl methyl cellulose;
        and wherein the nanoparticles are solid lipid nanoparticles (SLN) in a dispersion form in an amount from 0.10 to 10 wt. %;
    and wherein the nanoparticles comprise;
        20 to 99 w/w parts of a solid lipid selected from the group consisting of natural plant or synthetical wax;
        0.01 to 20 w/w parts d-α-Tocopheryl polyethylene glycol 1000 succinate (TPGS);
        red palm oil concentrate comprising 30% tocotrienols in an amount up to 20 wt. % of the total lipid content; and
        0.00001 to 70 w/w parts of an active substance;
        wherein the nanoparticles have a diameter of 15-100 nm.

2. The mucoadhesive dispersion nanoparticle system, according to claim 1, wherein the hydroxypropyl methyl cellulose has a viscosity of from 2500 to 5500 cps (mPa·s).

3. The mucoadhesive dispersion nanoparticle system according to claim 1, wherein the solid lipid in the composition of the solid lipid nanoparticles (SLN) is carnauba wax.

4. The mucoadhesive dispersion nanoparticle system according to claim 1, wherein the aqueous medium further comprises buffers, isotonic salts and preservatives.

5. The mucoadhesive dispersion nanoparticle system according to claim 1, wherein the solid lipid nanoparticles (SLN) further comprises 0.01 to 10 w/w parts a polysorbate selected from a group consisting of polysorbate 20, polysorbate 40, polysorbate 60 or polysorbate 80.

6. The mucoadhesive dispersion nanoparticle system according to claim 5, wherein the polysorbate is polysorbate 40.

7. The mucoadhesive dispersion nanoparticle system according to claim 1, characterized in that the active substance incorporated into the core of the solid lipid nanoparticle (SLN) is selected from pharmaceutically active compounds, diagnostic agents, biological products, food supplements, cosmetics and medical devices.

8. A method for producing the mucoadhesive dispersion nanoparticle system according to claim 1, characterized in that the hydroxypropyl methyl cellulose is dissolved in water to form an aqueous solution; and the resultant aqueous solution is cooled down gradually by stirring to 20° C.+/−2° C.; and further characterized in that the dispersion of the solid lipid nanoparticles is prepared by mixing the lipid compound, d-α-Tocopheryl polyethylene glycol 1000 succinate (TPGS), red palm oil concentrate with contents of 30% tocotrienols and the active substance, the resultant mixture is heated to 90° C.+/−2° C. in order to melt it, it is stirred until homogenization after which water is added to the resultant mixture with stirring at 90° C.+/−2° C.

* * * * *